United States Patent
Yamamoto

(10) Patent No.: US 8,657,729 B2
(45) Date of Patent: Feb. 25, 2014

(54) METHOD OF FOLDING ABSORBENT ARTICLE

(75) Inventor: Hiroki Yamamoto, Kanonji (JP)

(73) Assignee: Unicharm Corporation, Ehime (JP)

( * ) Notice: Subject to any disclaimer, the term of this patent is extended or adjusted under 35 U.S.C. 154(b) by 334 days.

(21) Appl. No.: 12/743,937

(22) PCT Filed: Mar. 2, 2010

(86) PCT No.: PCT/JP2010/053734
§ 371 (c)(1), (2), (4) Date: Mar. 8, 2011

(87) PCT Pub. No.: WO2010/101277
PCT Pub. Date: Sep. 10, 2010

(65) Prior Publication Data
US 2011/0167765 A1    Jul. 14, 2011

(30) Foreign Application Priority Data
Mar. 2, 2009   (JP) ................ P2009-048423

(51) Int. Cl.
*B31B 1/26* (2006.01)
(52) U.S. Cl.
USPC ............. 493/416; 493/405; 493/408; 53/447; 53/429; 53/117
(58) Field of Classification Search
USPC ........... 493/405, 408, 416; 53/429, 443, 447, 53/147, 531, 111 R, 116–117
See application file for complete search history.

(56) References Cited

U.S. PATENT DOCUMENTS

| | | | | |
|---|---|---|---|---|
| 3,552,736 A | * | 1/1971 | Frick et al. | 493/331 |
| 3,774,903 A | * | 11/1973 | Sjoman et al. | 493/428 |
| 3,782,714 A | * | 1/1974 | Spencer et al. | 493/250 |
| 6,022,432 A | | 2/2000 | Elsberg et al. | |
| 6,077,379 A | * | 6/2000 | Herrin et al. | 156/269 |

(Continued)

FOREIGN PATENT DOCUMENTS

| CN | 1156262 C | 8/1997 |
|---|---|---|
| CN | 1156262 C | 7/2004 |

(Continued)

OTHER PUBLICATIONS

International Search Report for PCT/JP2010/053734 mailed Jul. 20, 2010.

(Continued)

*Primary Examiner* — Christopher Harmon
(74) *Attorney, Agent, or Firm* — Lowe Hauptman & Ham LLP

(57) ABSTRACT

A method (1) includes: a step (S10) of conveying the wearing article (1) in such a manner that a front waistline portion (10) and a back waistline portion (20) extend in a conveyance direction (MD) of the wearing article (1); a step (S20) of changing the conveyance direction (MD) of the wearing article (1) by 90 degrees; a step (S30) of folding a flap portion (70) toward the front waistline portion (10), while conveying the wearing article (1); a step (S40) of folding the wearing article (1) along a middle portion, which is located in the middle between the front waistline portion (10) and a crotch portion (30) in the front-to-back direction of the wearing article (1), in such a manner that the front waistline portion (10) and the crotch portion (30) face each other.

6 Claims, 4 Drawing Sheets

(56) References Cited

U.S. PATENT DOCUMENTS

| | | | |
|---|---|---|---|
| 6,113,717 A * | 9/2000 | Vogt et al. | 156/73.1 |
| 6,482,278 B1 * | 11/2002 | McCabe et al. | 156/73.1 |
| 6,730,188 B2 * | 5/2004 | Sanders | 156/256 |
| 6,913,664 B2 | 7/2005 | Umebayashi et al. | |
| 7,374,627 B2 * | 5/2008 | McCabe | 156/73.1 |
| 7,708,849 B2 * | 5/2010 | McCabe | 156/73.1 |
| 8,273,003 B2 * | 9/2012 | Umebayashi et al. | 493/417 |
| 2002/0174930 A1 | 11/2002 | Umebayashi et al. | |
| 2006/0218700 A1 | 10/2006 | Uda | |
| 2007/0043331 A1 | 2/2007 | Haruki et al. | |
| 2008/0099130 A1 | 5/2008 | Umebayashi et al. | |
| 2008/0223537 A1 | 9/2008 | Weidmann | |
| 2012/0324633 A1 * | 12/2012 | Back et al. | 2/400 |

FOREIGN PATENT DOCUMENTS

| | | |
|---|---|---|
| CN | 1826092 A | 8/2006 |
| JP | 11113956 | 4/1994 |
| JP | H07-125837 A | 5/1995 |
| JP | 11113956 A | 4/1999 |
| JP | 2001-019070 | 1/2001 |
| JP | 2003098110 A | 4/2003 |
| JP | 2003250826 A | 9/2003 |
| JP | 2005230330 | 9/2005 |
| WO | 2006068081 | 6/2006 |

OTHER PUBLICATIONS

Office Action issued on Mar. 7, 2013 in the counterpart CO Patent Aapplication No. 11-126460.
Office Action issued on Apr. 1, 2013 in the counterpart CN Patent Application No. 201080010133.7.
Office Action issued on Apr. 23, 2013 in the counterpart JP Patent Application No. 2009-048423.
Search Report issued in European Application No. 10748868.6, dated Dec. 6, 2012, 6 pages.
Office Action issued on Mar. 7, 2013 for counterpart Colombian Patent Application File No. 11 126460.
Office Action issued on Apr. 1, 2013 for counterpart Chinese Patent Application No. 201080010133.7.
Office Action issued on Apr. 23, 2013 for counterpart Japanese Patent Application No. 11 121351.
Office Action issued May 31, 2013 corresponds to EA patent application No. 201101250.
Office Action issued on Jul. 17, 2013 corresponds to Egyptian patent application No. 1462/2011.
Office Action issued Nov. 8, 2013, corresponds to Eurasian patent application No. 201101250.

* cited by examiner

FIG. 4
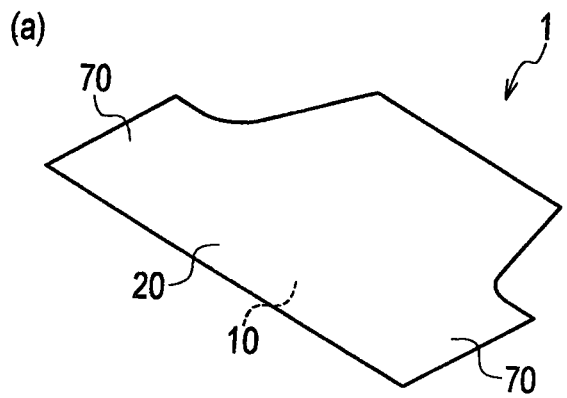
(a)
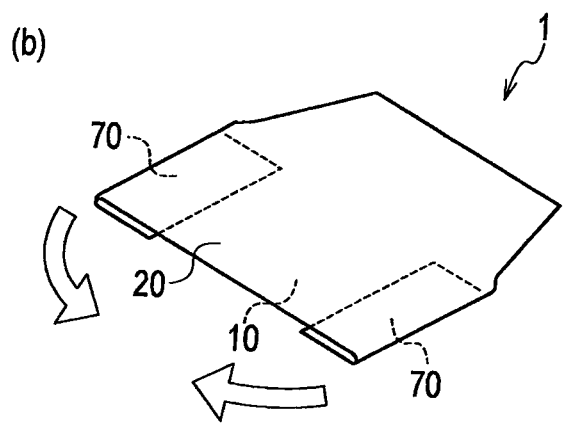
(b)
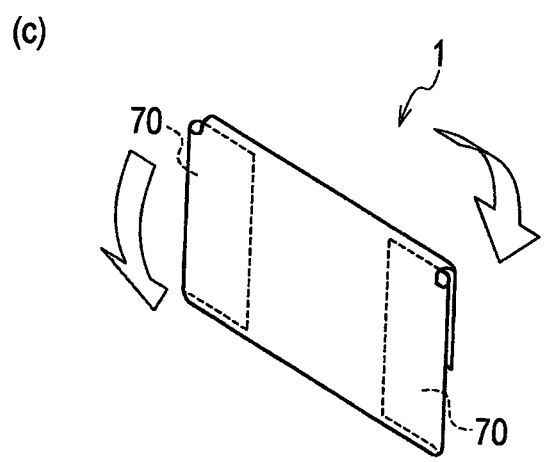
(c)

METHOD OF FOLDING ABSORBENT ARTICLE

RELATED APPLICATIONS

The present application National Phase of PCT/JP2010/053734 filed Mar. 2, 2010, and claims priority from, Japanese Application Number 2009-048423, filed Mar. 2, 2009, the disclosures of which are hereby incorporated by reference herein in their entirety.

TECHNICAL FIELD

The present disclosure relates to a method of folding an absorbent article.

BACKGROUND ART

An absorbent article, such as a pants-type diaper, generally includes a front waistline portion to be fitted to the front waistline of a wearer, a back waistline portion to be fitted to the back waistline of the wearer, and a crotch portion to be fitted to the crotch of the wearer.

Leg-surrounding openings into which the legs of the wearer are inserted are formed at both sides of the crotch portion.

Protruding portions (so-called flap portions) are formed in the course of the formation of the leg-surrounding openings. Specifically, the protruding portions are formed in the front waistline portion and the back waistline portion, and protrude outward relative to the crotch portion in a direction perpendicular to a front-to-back direction from the front waistline portion toward the back waistline portion.

Such an absorbent article is folded more than once, and multiple folded absorbent articles are collectively packaged.

The inventors are aware an exemplary method of folding an absorbent article, in which the flap portions are firstly folded toward the front waistline portion or the back waistline portion.

Then, the absorbent article is folded in the middle, in the front-to-back direction of the absorbent article, between the front waistline portion and the crotch portion or between the back waistline portion and the crotch portion, in such a manner that the front waistline portion and the crotch portion face each other or the back waistline portion and the crotch portion face each other (see Patent Literature 1, for example).

Meanwhile, a lengthwise conveying method and a crosswise conveying method have generally been known as suitable for conveying an absorbent article being manufactured.

In the lengthwise conveying method, the front waistline portion and the back waistline portion are conveyed in such a manner as to extend in a cross direction perpendicular to a conveyance direction of the absorbent article.

By contrast, in the crosswise conveying method, the front waistline portion and the back waistline portion are conveyed in such a manner as to extend in the conveyance direction of the absorbent article.

The inventors have discovered that, the aforementioned conventional method of folding an absorbent article has the following problem.

In the lengthwise conveying method, the absorbent article is laid to extend in the conveyance direction and has a shape symmetrical with respect to a center line in the cross direction of the absorbent article.

By contrast, in the crosswise conveying method, the absorbent article has a shape asymmetrical with respect to the center line in the cross direction of the absorbent article.

Accordingly, in order to achieve desired folding, the crosswise conveying method might require necessarily involves more complicated steps than the lengthwise conveying method does.

CITATION LIST

Patent Literature

PTL 1: Japanese Patent Application Publication No. 2001-19070 (pp. 2 to 4, FIGS. 1 to 3)

SUMMARY

It is desirable to provide a method of folding an absorbent article which is capable of achieving desired folding without complicated steps when the absorbent article is conveyed by the crosswise conveying method.

A first aspect of the present invention is Summarized as a method of folding an absorbent article including a front waistline portion to be fitted to a front waistline of a wearer; a back waistline portion to be fitted to a back waistline of the wearer; a crotch portion to be fitted to a crotch of the wearer; and a protruding portion defined by the front waistline portion and/or the back waistline portion and protruding outward relative to the crotch portion in a transverse direction perpendicular to a front-to-back direction from the front waistline portion toward the back waistline portion, the method comprising: conveying the absorbent article in such a manner that the front waistline portion and the back waistline portion extend in a conveyance direction of the absorbent article; changing the conveyance direction of the absorbent article by 90 degrees; folding the protruding portion toward the front waistline portion, while conveying the absorbent article after the conveyance direction of the article absorbent has been changed; folding the absorbent article along a middle portion between the front waistline portion and the crotch portion in the front-to-back direction of the absorbent article, in such a manner that the front waistline portion and the crotch portion face each other.

According to the aspect of the present invention, there can be provided a method of folding an absorbent article which is capable of achieving desired folding without complicated steps when the absorbent article is conveyed by the crosswise conveying method.

BRIEF DESCRIPTION OF DRAWINGS

FIG. 4 (*a*) to FIG. 4 (*c*) are perspective views of an absorbent article which is being folded by the method of FIG. 3.

DETAILED DESCRIPTION

Hereinafter, a method of folding an absorbent article according to one or more embodiment of the present invention will be described with reference to the accompanying drawings.

Note that, in the following description of the drawings, same or similar reference signs denote same elements and portions. In addition, it should be noted that the drawings are schematic and are not to scale unless otherwise specified. Therefore, specific dimensions and the like should be determined in consideration of the following description. Moreover, the drawings do not necessarily reflect the real-life dimensional relationships and ratios of components.

First, a structure of an absorbent article 1 according to one or more embodiments will be described with reference to FIG. 1 which is a partially cutaway perspective view showing the absorbent article 1. In the particularly illustrated embodiment, the absorbent article 1 is a pants-type disposal diaper for adults.

Figure 1:
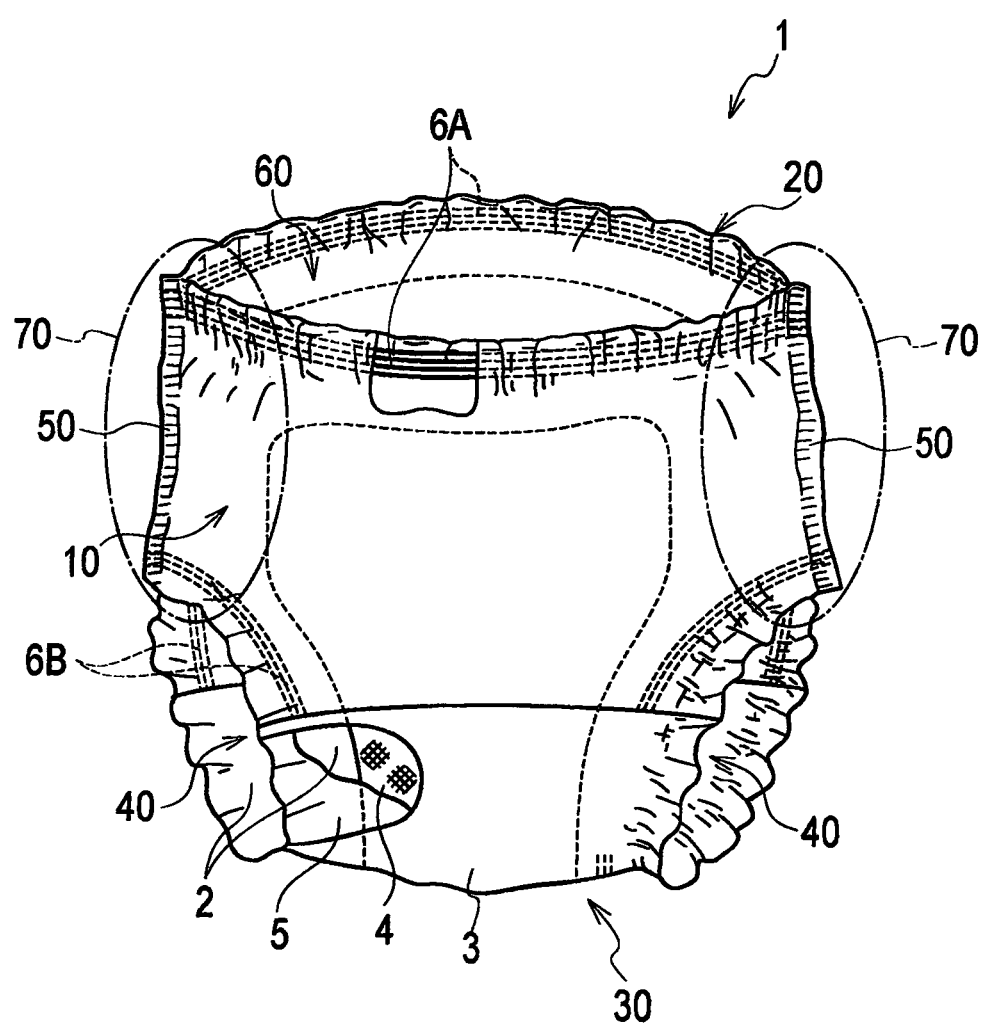
FIG. 1 is a partially cutaway perspective view of an absorbent article according to one or more embodiment of the present invention.

As shown in FIG. 1, the absorbent article 1 is formed mainly of a top sheet 2, a bottom sheet 3, an absorber 4 and a waterproof sheet 5.

The top sheet 2 is configured to come into contact with a skin of a person wearing the absorbent article 1 (hereinafter, referred to as "wearer"). As the top sheet 2, a liquid-permeable sheet, such as a non-woven fabric or a perforated plastic film, is used.

The back sheet 3 is provided outside the top sheet 2, in other words, the back sheet 3 is provided at the side farther from the wearer than top sheet 2. As the back sheet 3, a non-woven fabric or the like is used.

The absorber 4 is provided between the top sheet 2 and the back sheet 3, and is configured to absorb excretion of the wearer. As the absorber 4, a mixture of comminuted wood pulp and superabsorbent polymer particles, or the like, is used.

The waterproof sheet 5 is provided between the back sheet 3 and the absorber 4, and does not allow excretion of the wearer to permeate therethrough. The waterproof sheet 5 is made of a liquid-impermeable sheet.

The absorbent article 1 as described above is formed by combining: a front waistline portion 10 to be fitted to the front waistline of the wearer; a back waistline portion 20 to be fitted to the back waistline of the wearer; and the crotch portion 30 to be fitted to the crotch of the wearer.

Note that, leg-surrounding openings 40 are formed respectively at sides of the crotch portion 30, and the legs of the wearer are to be inserted through the leg-surrounding openings 40.

The front waistline portion 10 and the back waistline portion 20 are united by joint portions 50, and thus form a waistline opening 60 to be fit around the body of the wearer.

Flap portions 70 (protruding portions) are each formed of the front waistline portion 10 and the back waistline portion 20, and protrude outward relative to the crotch portion 30 in a transverse direction perpendicular to a front-to-back (longitudinal) direction from the front waistline portion 10 toward the back waistline portion 20. Note that the flap portions 70 include the joint portions 50, respectively.

A waist gather 6A made of rubber strands or the like having stretchability is provided in the peripheral edges of the front waistline portion 10 and the back waistline portion 20.

For example, the front waistline portion 10 and the back waistline portion 20 may be provided with the waist gather 6A to be thus stretchable in a cross direction crossing a front-to-back direction extending from the front waistline portion 10 to the back waistline portion 20, or may themselves be formed of sheets having stretchability to be thus stretchable in the cross direction.

The crotch portion 30 is provided between the front waistline portion 10 and the back waistline portion 20.

Leg gathers 6B each made of rubber strands or the like having stretchability are provided respectively at the sides of the crotch portion 30.

For example, the crotch portion 30 may be provided with the leg gathers 6B to be thus stretchable in the front-to-back direction of the absorbent article 1, or may itself be formed of a sheet having stretchability to be thus stretchable in the front-to-back direction of the absorbent article 1.

Next, a method of manufacturing the absorbent article 1 according to the first embodiment of the present invention will be described with reference to FIG. 2 which is an explanatory view for explaining a relevant part of the method of manufacturing the absorbent article.

Figure 2:
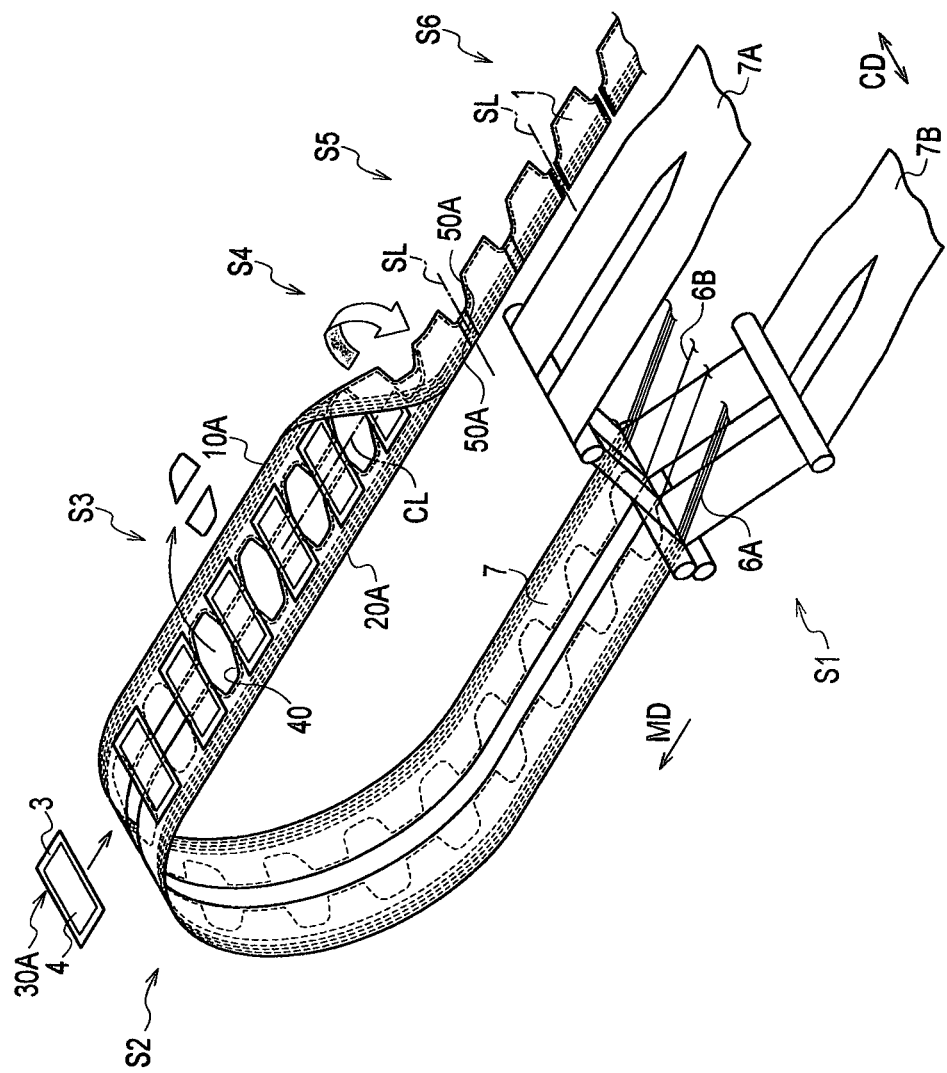
FIG. 2 is a diagram for explaining a relevant part of a method of manufacturing an absorbent article according to one or more embodiment of the present invention.

As shown in FIG. 2, the method of manufacturing the absorbent article 1 includes at least a waistline forming step S1, an absorber transferring step S2, a leg-surrounding opening forming step S3, a folding step S4, a joining step S5, and a cutting step S6.

In the waistline forming step S1, a web 7 is formed by disposing gathers (the waist gather 6A and/or the leg gathers 6B) between a web 7A and a web 7B. The web 7 is to be processed into the front waistline portion 10 and the back waistline portion 20.

Note that, the web 7 (the webs 7A and 7B) being conveyed is stretchable in a cross direction CD (a width direction) orthogonal to a conveyance direction MD (Machine Direction) of the web 7.

In addition, the web 7 is asymmetrical with respect to a center line CL that bisects a width in the cross direction CD of the web 7 and extends in the conveyance direction MD of the web 7.

In the absorber transferring step S2, a crotch portion member 30A to be processed into the crotch portion 30 is transferred onto the web 7, specifically, between the front waistline portion 10 and the back waistline portion 20, after the waistline forming step S1. Note that, the crotch portion member 30A is formed of the back sheet 3 and the absorber 4.

In the leg-surrounding opening forming step S3, the leg-surrounding openings 40 (so-called leg holes) are formed by cutting the web 7 (the webs 7A and 7B) after the absorber transferring step S2.

Note that, the leg-surrounding openings 40 are not necessarily formed by cutting only the web 7 (the webs 7A and 7B), but may alternatively be formed by cutting the back sheet 3 forming the crotch portion member 30A together with the web 7A and the web 7B.

Here, the absorber transferring step S2 and the leg-surrounding forming step S3 may be performed in the reverse order.

In the folding step S4, the web 7 is folded in half along a folding line extending in the conveyance direction MD of the web 7, by bringing a side edge 10A of the front waistline portion 10 in the web 7 toward a side edge 20A of the back waistline portion 20 in the web 7, after the leg-surrounding opening forming step S3.

Note that, in the particularly illustrated embodiment, the folding line is the same as the center line CL. Moreover, the folding line does not necessarily coincide with the center line CL, and may be offset from the center line CL toward the side edge 10A or toward the side edge 20A.

In the joining step S5, the folded parts of the web 7 are joined at joint regions 50A to be processed into the joint portions 50 of the absorbent article 1 by an ultrasonic treatment or a heat treatment, after the folding step 34.

Note that the joint regions 50A respectively indicate regions at both sides of an imaginary line SL in the conveyance direction MD. The imaginary line SL indicates a cutting line extending in the cross direction CD.

In the cutting step S6, the web 7 in which the joint regions 50A have been joined is cut along the imaginary line SL after the joining step S5. As a result, the absorbent article 1 is manufactured.

Next, a method of folding an absorbent article according to one or more embodiment of the present invention will be explained with reference to FIGS. 3-4.

Figure 3:
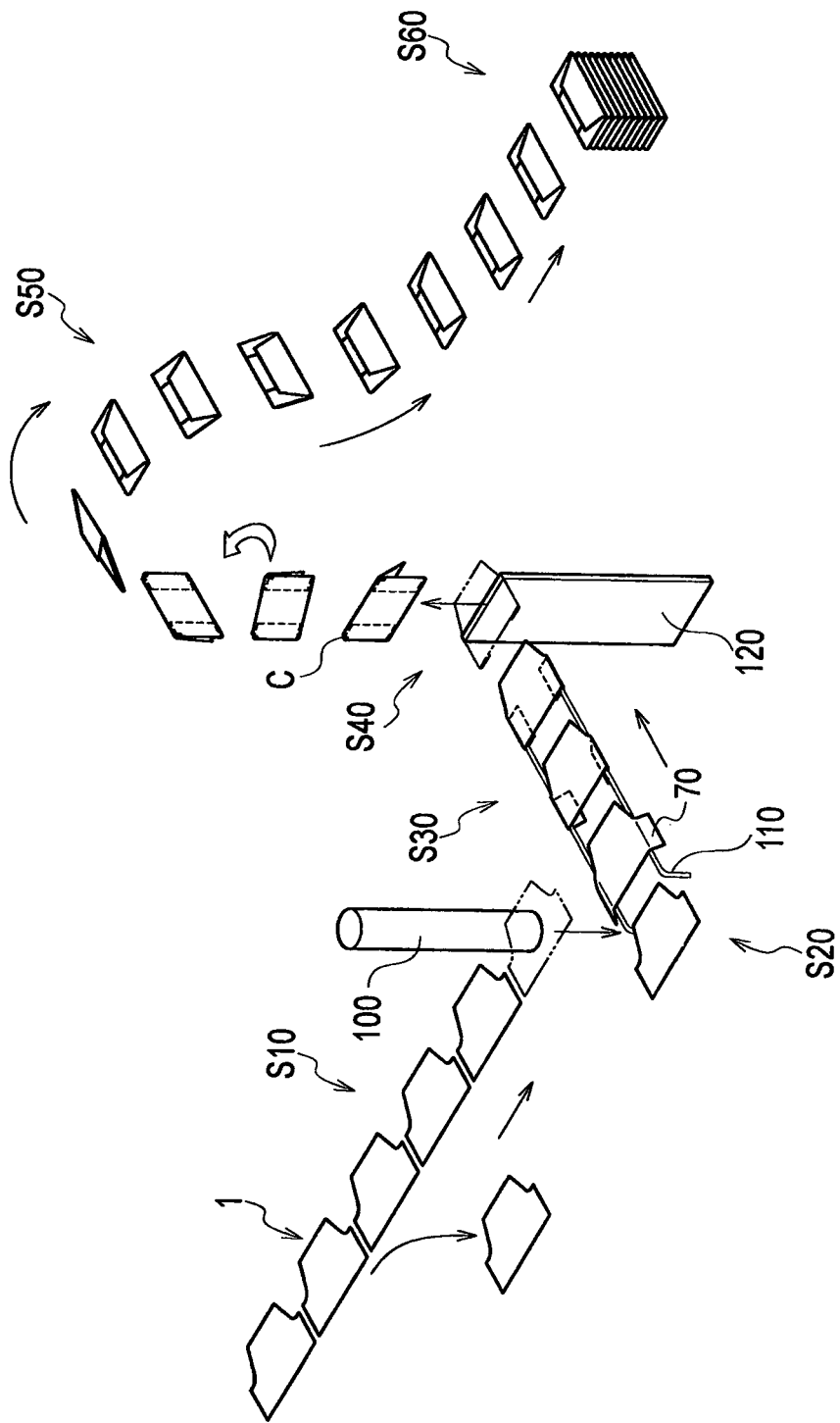
FIG. 3 is a diagram for explaining a relevant part of a method of folding an absorbent article according to one or more embodiment of the present invention.

FIG. 3 is a diagram for explaining a relevant part of the method of folding an absorbent article. FIG. 4 (*a*) to FIG. 4 (*c*) are perspective views of the absorbent article 1 which is being folded by the method of FIG. 3.

Note that the absorbent article 1 to be folded has been determined to have no manufacturing defect after the cutting step S6 described above.

As shown in FIG. 3, the method of folding an absorbent article includes: at least an article conveying step S10; a conveyance direction changing step S20; a flap folding step S30; a middle-portion folding step S40; an article reorienting step S50; and a packaging step S60.

In the article conveying step S10, the absorbent article 1 determined to have no manufacturing defect is conveyed. Specifically, the absorbent article 1 is conveyed by a first conveyor belt (not illustrated) in such a manner that the front waistline portion 10 and the back waistline portion 20 extend in the conveyance direction MD of the absorbent article 1. This is the crosswise conveying method.

Here, the absorbent article 1 is conveyed in a state where the front waistline portion (first/second portion) 10 faces downward and the back waistline portion (second/first portion) 20 faces upward.

In the conveyance direction changing step S20, the conveyance direction MD of the absorbent article 1 is changed, e.g., by 90°. In other words, the conveying method of the absorbent article 1 is changed by the conveyance direction changing step S20 from the crosswise conveying method (e.g., in the article conveying step S10) to the lengthwise conveying method (e.g., in the flap folding step S30 to be described herein below).

The downward-thrust mechanism 100 includes a servomotor, a cam and a pressing unit (not illustrated) which can be moved up and down. The downward-thrust mechanism 100 transmits a signal to the servomotor corresponding to the conveyance interval of the absorbent article 1. Rotation of the servomotor is transferred to the pressing unit by the cam and thus the pressing unit goes up and down.

Specifically, the absorbent article 1 is thrust downward off the original conveyance path of the first conveyor belt by a downward-thrust mechanism 100. Subsequently, the absorbent article 1 is conveyed by a second conveyor belt (not shown) in a state where the conveyance direction MD of the absorbent article 1 has been changed by 90°.

In the flap folding step S30, while the absorbent article 1 the conveyance direction MD of which has been changed is conveyed, the flap portions 70 are folded toward the front waistline portion 10.

Specifically, the absorbent article 1 is conveyed by the second conveyor belt (not illustrated) while being sucked and held on the belt. The conveyor belt sucks and holds the back waistline portion 20, and conveys the absorbent article 1 with the front waistline portion 10 facing downward. The conveyor belt (not illustrated) is a suction belt having a suction mechanism and sucks at least a part of the back waistline portion 20.

While the absorbent article 1 is conveyed by the second conveyor belt, the flap portions 70 hanging downward are folded toward the front waistline portion 10 by a side-portion guide mechanism 110. In sum, the absorbent article 1 changes from a state shown in FIG. 4 (*a*) to a state shown in FIG. 4 (*b*).

In the middle-portion folding step S40, the absorbent article 1 is folded along a middle portion C in such a manner that the front waistline portion 10 and the crotch portion (third portion) 30 face each other.

The side-portion guide mechanism 110 includes a bar-like member supporting a portion inside of the flap portions 70 of the absorbent article 1. Since the absorbent article 1 is conveyed by a suction conveyor (not illustrated) in a state that at least the part of the back waistline portion 20 is sucked, the outside of the flap portions 70 is not sucked and thus it hangs down. The hanged flap portions 70 is folded over the front waistline portion 10 using a bending plate. Here, the middle portion C is located between the front waistline portion 10 and the crotch portion 30 in the front-to-back direction of the absorbent article 1.

Any portion may be selected as the middle portion C, as long as the portion is located approximately in the middle between the front waistline portion 10 and the crotch portion 30 in the front-to-back direction of the absorbent article 1.

Specifically, the absorbent article 1 is thrust at its middle portion C upward from the conveyance path of the second conveyor by an upward-thrust mechanism 120.

Similar to the downward-thrust mechanism 100, the upward-thrust mechanism 120 includes a servomotor, a cam and an upward-thrust unit (not illustrated) which can be moved up and down. The upward-thrust mechanism 120 transmits a signal to the servomotor corresponding to the conveyance interval of the absorbent article 1. Rotation of the servomotor is transferred to the upward-thrust unit by the cam and thus the upward-thrust unit goes up and down.

In this event, the upward-thrust mechanism 120 thrusts the absorbent article 1 at the middle portion C on the side of the front waistline portion 10 toward which the flap portions 70 of the absorbent article 1 have been folded.

With this thrust, the absorbent article 1 with the flap portions 70 folded is further folded into two. In other words, the absorbent article 1 changes from the state shown in FIG. 4 (*b*) to a state shown in FIG. 4 (*c*).

In the article reorienting step S50, the absorbent article 1 thrust upward in the middle-portion folding step S40 is conveyed upward while being reoriented, for example, by 90° in the cross direction CD.

In the article reorienting step S50, the absorbent article 1 thrust upward in the middle-portion folding step S40 and thus folded is conveyed in a state that it is nipped by two belts, both of which are reoriented, and the absorbent article 1 is redirected by 90° during conveyance.

The absorbent article 1 is still conveyed while the conveyance direction MD of the absorbent article 1 is changed downward. Here, the crotch portion 30 of the absorbent article 1 is oriented toward the upstream in the conveyance direction MD of the absorbent article 1.

In the packaging step S60, multiple absorbent articles 1 are stacked and collectively packaged in a package (not illustrated).

In the embodiments) described above, the conveyance direction MD of the absorbent article 1 is changed by 90°, and the flap portions 70 are folded toward the front waistline portion 10 while the absorbent article 1 the conveyance direction MD of which has been changed is conveyed.

Then, the absorbent article 1 is folded along the middle portion C between the front waistline portion 10 and the crotch portion 30 in the front-to-back direction of the absorbent article 1, in such a manner that the front waistline portion 10 and the crotch portion 30 face each other.

With this folding method, the absorbent article 1 can be folded twice while being conveyed, the absorbent article 1 having a shape asymmetrical with respect to the center line in the cross direction CD of the absorbent article 1. This enables desired folding without complicated steps when the absorbent article 1 is conveyed by the crosswise conveying method.

In the embodiments) disclosed above, the absorbent article 1 is conveyed with the back waistline portion 20 facing upward in the article conveying step S10.

This allows the absorbent article 1 to be folded into a state where a helper who helps the wearer wear the absorbent article 1 can see an abdomen side ranging from the front waistline portion 10 to the crotch portion 30 when opening the folded absorbent article 1.

For this reason, the helper can help the wearer wear the absorbent article 1 while facing the wearer. In sum, this folding method allows the absorbent article 1 to be folded so that the helper can easily help the wearer wear the absorbent article 1.

In the embodiments) disclosed above, the absorbent article 1 is thrust downward off the original conveyance path of the absorbent article 1 in the conveyance direction changing step S20.

For example, in a case where the absorbent article 1 is thrust upward from the original conveyance path of the absorbent article 1, i.e., against gravity, it is necessary to press the whole area of the absorbent article 1 upward.

By contrast, the absorbent article 1 can be thrust downward and/or allowed to drop without defying gravity. In sum, it is not necessary, although not excluded, to press the whole area of the absorbent article 1 downward. Therefore, the conveyance direction MD of the absorbent article 1 can be changed without a complicated apparatus.

In the embodiment (s) disclosed above, the absorbent article 1 is conveyed with the front waistline portion 10 facing downward in the flap folding step S30 and the flap portions 70 hanging downward due to gravity in the flap folding step S30. In comparison with a case where the flap portions 70 are raised upward, the flap portions 70 can be easily folded by utilizing gravity without a complicated apparatus, while the folding accuracy is stabilized.

In the embodiment (s) disclosed above, in a state where the flap portions 70 hang downward, the flap portions 70 are folded toward the front waistline portion 10 in the flap folding step S30.

That is, the second conveyor belt sucks and holds the back waistline portion 20, and conveys the absorbent article 1 with the front waistline portion 10 facing downward.

This allows the absorbent article 1 to be conveyed stably, since the area is generally larger on the back waistline portion 20 side than on the front waistline portion 10 side. Therefore, the flap portions 70 can be easily folded by utilizing gravity while the folding accuracy is stabilized.

In the embodiment (s) disclosed above, the absorbent article 1 is thrust upward from the conveyance path of the absorbent article 1 in the middle-portion folding step S40.

If the absorbent article 1 is thrust downward off the conveyance path of the absorbent article 1, it is not possible to fold the absorbent article 1 into the state where the helper can see the abdomen side of the absorbent article 1 when opening the folded absorbent article 1.

After the middle-portion folding step S40 and the article reorienting step S50, in the packaging step S60, h multiple absorbent articles 3 are collectively packaged.

This makes it possible to keep the absorbent article 1 folded with the flap portions 70 placed inward, and to inhibit the flap portions 70 from opening during the subsequent steps.

Accordingly, the multiple absorbent articles 1 can be stacked one on another, and then be packaged with the absorbent articles 1 orderly arranged in the respective packages (not illustrated).

Further Embodiments

As described above, the details of several embodiments of the present invention have been exemplarily disclosed. It should not be understood that the description and drawings which constitute part of this disclosure limit the present invention. Based on this disclosure, those skilled in the art may easily come up with various alternative embodiments, examples and operation techniques.

For example, the following additional embodiments can be envisaged. Specifically, the absorbent article 1 has been described as including, in combination, the front waistline portion 10, the back waistline portion 20 and the crotch portion 30.

The absorbent article 1 is not limited to this configuration but may be formed entirely as a single unit. In this case, needless to say, a different method of manufacturing an absorbent article is employed.

The method of folding an absorbent article 1 has been described as for folding a pants-type disposable diaper. The method is not limited to such use, but may be used for folding an open-type disposable diaper, or any other wearing article, for example.

The description has been given that the flap portions are defined by both the front and back waistline portions 10, 20. However, the flap portions may be defined by only the front waistline portion 10 or only the back waistline portion 20. For example, an open-type diaper in some embodiments includes only flap portions in the back waistline portion 20 for carrying fasteners. In further embodiments, the flap portions are separate pieces attached to the front waistline portion 10 and/or the back waistline portion 20.

The method of folding an absorbent article 1 has been described as including the steps (S10 to S60). The method is not limited to this arrangement, and does not necessarily include, for example, the article reorienting step S50 and/or the packaging step S60.

The description has been given that the absorbent article 1 is conveyed with the back waistline portion 20 facing upward in the article conveying step S10. The article conveying step S10 is not limited to this arrangement, and the absorbent article 1 may be conveyed with the back waistline portion 20 facing downward.

The description has been given that the absorbent article 1 is thrust downward off the original conveyance path of the absorbent article 1 in the conveyance direction changing step S20. The conveyance direction changing step S20 is not limited to this arrangement, and the absorbent article 1 may be thrust upward from the original conveyance path of the absorbent article 1. In some embodiments, the absorbent article 1 is not thrust. Instead, the absorbent article 1 is allowed to drop onto the second belt conveyor, or is smoothly transferred from the first to the second conveyor belt.

The description has been given that the conveyance direction changing step S20 does not change the upward facing side of the absorbent article 1, i.e., the back waistline portion 20 (or the front waistline portion 10) faces upward both before (i.e., in the article conveying step S10) and after (in the flap folding step S30) the conveyance direction changing step S20. However, the conveyance direction changing step S20 is not limited to this arrangement, and may change the upward facing side of the absorbent article 1, e.g., the back waistline portion 20 faces upward before (i.e., in the article conveying step S10) the conveyance direction changing step S20, but the front waistline portion 10 faces upward after (i.e., in the flap folding step S30) the conveyance direction changing step S20, and vice versa.

The description has been given that the absorbent article 1 is conveyed with the front waistline portion 10 facing downward in the flap folding step S30. The flap folding step S30 is not limited to this arrangement, and the absorbent article 1 may be conveyed with the front waistline portion 10 facing upward.

The description has been given that the flap portions 70 are folded toward the front waistline portion 10. However, the flap folding step S30 is not limited to this arrangement, and the flap portions 70 may be folded toward the back waistline portion 20.

The description has been given that the flap portions 70 on both sides are folded. However, the flap folding step S30 is not limited to this arrangement, and the flap portion 70 on only one side may be folded alone.

The description has been given that the absorbent article 1 is thrust upward in the middle-portion folding step S20. The conveyance direction changing step S20 is not limited to this arrangement, and the absorbent article 1 may be thrust and/or dropped downward and/or smoothly transfer to a subsequent conveyor belt.

According to one or more of the disclosed aspects of the present invention, there can be provided a method of folding an absorbent article which is capable of achieving desired folding without complicated steps when the absorbent article is conveyed by the crosswise conveying method.

As described above, the present invention naturally includes various embodiments which are not described herein. Accordingly, the technical scope of the present invention should be determined only by the elements of the invention in the scope of claims regarded as appropriate based on the description.

According to the aspect of the present invention, there can be provided a method of folding an absorbent article 1 which is capable of achieving desired folding without complicated steps when the absorbent article is conveyed by the crosswise conveying method. The entire content of Japanese Patent Application 2009-048423 (filed on Mar. 2, 2009) is incorporated herein by reference.

INDUSTRIAL APPLICABILITY

Therefore, according to the present invention, since it is possible to provided a method of folding an absorbent article which is capable of achieving desired folding without complicated steps when the absorbent article is conveyed by the crosswise conveying method, it is useful in manufacturing technology for absorbent articles.

REFERENCE SIGNS LIST 1 absorbent article
2 top surface sheet
3 bottom surface sheet
4 absorber
5 waterproof sheet
6A waist gather
6B leg gather
7, 7A, 7B web
10 front waistline portion
10A side edge
20 back waistline portion
20A side edge
30 crotch portion
30A crotch portion member
40 leg-surrounding openings
50 joint portion
50A joint region
60 waist openings
70 flap portion
100 downward-thrust mechanism
110 side-portion guide mechanism
120 upward-thrust mechanism

The invention claimed is:

1. A method of folding an absorbent article including a front waistline portion to be fitted to a front waistline of a wearer; a back waistline portion to be fitted to a back waistline of the wearer; a crotch portion to be fitted to a crotch of the wearer; and a protruding portion defined by the front waistline portion and/or the back waistline portion and protruding outward relative to the crotch portion in a transverse direction perpendicular to a front-to-back direction from the front waistline portion toward the back waistline portion, the method comprising:

conveying the absorbent article in such a manner that the front waistline portion and the back waistline portion extend in a conveyance direction of the absorbent article;

changing the conveyance direction of the absorbent article by 90 degrees;

folding the protruding portion toward the front waistline portion, while conveying the absorbent article after the conveyance direction of the article absorbent has been changed;

folding the absorbent article along a middle portion between the front waistline portion and the crotch portion in the front-to-back direction of the absorbent article, in such a manner that the front waistline portion and the crotch portion face each other, wherein in said folding the absorbent article, the absorbent article is thrust upward from the conveyance path of the absorbent article.

2. The method according to claim 1, wherein
in said conveying, the absorbent article is conveyed with the back waistline portion facing upward.

3. The method according to claim 1, wherein
in said changing, the absorbent article is thrust downward off a conveyance path of the absorbent article.

4. The method according to claim 1, wherein
in said folding the protruding portion, the absorbent article is conveyed with the front waistline portion facing downward.

5. The method according to claim 1, wherein
in said folding the protruding portion, while the protruding portion hangs downward, the protruding portion is folded toward the front waistline portion.

6. The method according to claim 1, further comprising collectively packaging a plurality of the folded absorbent articles.

* * * * *